US009132074B2

(12) United States Patent
Halpern et al.

(10) Patent No.: US 9,132,074 B2
(45) Date of Patent: *Sep. 15, 2015

(54) SUNSCREEN COMPOSITIONS HAVING SYNERGISTIC COMBINATION OF UV FILTERS

(71) Applicant: L'OREAL, Paris (FR)

(72) Inventors: Susan Halpern, Basking Ridge, NJ (US); Jean-Thierry Simonnet, Mamaroneck, NY (US); Anil Shah, East Windsor, NJ (US); Didier Candau, Bievres (FR); Angélina Roudot, Le Kremlin Bicetre (FR)

(73) Assignee: L'OREAL, Paris (FR)

( * ) Notice: Subject to any disclaimer, the term of this patent is extended or adjusted under 35 U.S.C. 154(b) by 148 days.

This patent is subject to a terminal disclaimer.

(21) Appl. No.: 13/719,328

(22) Filed: Dec. 19, 2012

(65) Prior Publication Data

US 2014/0170093 A1  Jun. 19, 2014

(51) Int. Cl.
| | |
|---|---|
| *A61Q 17/04* | (2006.01) |
| *A61K 8/35* | (2006.01) |
| *A61K 8/40* | (2006.01) |
| *A61K 8/46* | (2006.01) |
| *A61K 8/49* | (2006.01) |
| *A61K 8/58* | (2006.01) |

(52) U.S. Cl.
CPC . *A61K 8/585* (2013.01); *A61K 8/35* (2013.01); *A61K 8/40* (2013.01); *A61K 8/466* (2013.01); *A61K 8/4966* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 6,048,517 A | 4/2000 | Kaplan | |
| 6,171,579 B1 * | 1/2001 | Allard et al. | 424/59 |
| 7,014,842 B2 | 3/2006 | Dueva-Koganov et al. | |
| 8,557,227 B2 | 10/2013 | Simonnet et al. | |
| 2005/0013781 A1 | 1/2005 | Dueva-Koganov et al. | |
| 2007/0218022 A1 | 9/2007 | Richard et al. | |
| 2008/0305057 A1 | 12/2008 | Fox | |
| 2008/0317685 A1 | 12/2008 | Candau et al. | |
| 2009/0189090 A1 | 7/2009 | Meyer et al. | |
| 2009/0202459 A1 | 8/2009 | Spaulding | |
| 2009/0232754 A1 | 9/2009 | Meyer et al. | |
| 2010/0080764 A1 | 4/2010 | Fox | |
| 2010/0129303 A1 | 5/2010 | Dueva-Koganov et al. | |
| 2010/0303910 A1 | 12/2010 | Candolives et al. | |
| 2010/0316582 A1 * | 12/2010 | Tsuzuki et al. | 424/59 |
| 2011/0052516 A1 | 3/2011 | Mendrok-Edinger | |
| 2011/0268678 A1 | 11/2011 | Armstrong | |
| 2012/0015016 A1 | 1/2012 | Galdi et al. | |
| 2012/0237466 A1 | 9/2012 | Graham | |
| 2013/0129649 A1 | 5/2013 | Simonnet et al. | |
| 2013/0129650 A1 | 5/2013 | Simonnet et al. | |

FOREIGN PATENT DOCUMENTS

WO  WO-2010118415 A1  10/2010

OTHER PUBLICATIONS

Moyal, Dominique; Photodermatol Photoimmunol Photomed 20, p. 243-247, 2004.*
Chatelain et al. Photochem Photobiol 74(3), p. 401-406, 2001.*
Bissonnette, R.; Skin Therapy Letters 13(6), p. 5-7, 2008.*
U.S. Appl. No. 13/719,351, Halpern et al.
U.S. Appl. No. 13/719,368, Halpern et al.
U.S. Appl. No. 13/719,374, Halpern et al.
U.S. Appl. No. 13/719,393, Halpern et al.
Beasley et al. "Characterization of the UVA Protection Provided by Avobenzone, Zinc Oxide, and Titanium Dioxide in Broad-Spectrum Sunscreen Products." American Journal of Clinical Dermatology [online], Dec. 1, 2010 [Retrieved on Jan. 19, 2012], vol. 11, No. 6, Retrieved from the Internet: <URL: http://www.ingentaconnect.com/content/adis/derm/2010/00000011/00000006/art00006>, see entire document, especially p. 416, col. 2, para 3.
Notification of Transmittal of the International Search Report and the Written Opinion of the International Searching Authority, or the Declaration, International Application No. PCT/US2012/066050, mailed Feb. 8, 2013.
Notification of Transmittal of the International Search Report and the Written Opinion of the International Searching Authority, or the Declaration; International Search Report; Written Opinion of the International Searching Authority, International Application No. PCT/US2013/076465.

* cited by examiner

*Primary Examiner* — Nissa Westerberg
(74) *Attorney, Agent, or Firm* — Novak Druce Connolly Bove + Quigg LLP

(57) ABSTRACT

The disclosure relates to sunscreen compositions having a synergistic combination of ultraviolet light (UV) filtering agents that provide a high sun protection factor (SPF). Compositions according to the disclosure have high SPF values without requiring high overall amounts of UV filtering agents. Furthermore, the disclosure relates to methods of using the described compositions for protecting keratinous substances such as skin and hair from UV radiation.

20 Claims, No Drawings

SUNSCREEN COMPOSITIONS HAVING SYNERGISTIC COMBINATION OF UV FILTERS

FIELD OF THE DISCLOSURE

The present disclosure relates to sunscreen compositions comprising a synergistic combination of ultra violet ("UV") filters, and to methods of using the combination of UV filters to protect keratinous substrates such as skin and hair from UV radiation.

BACKGROUND

The negative effects of exposure to ultraviolet ("UV") light are well-known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to the cell membrane results in loss of cell permeability, increased intercellular ionic concentration, and decreased ability to excrete or detoxify waste products. The end result is a loss of skin elasticity and the appearance of wrinkles. This process is commonly referred to as photoaging.

Sunscreens can be used to protect against UV damage and delay the signs of aging. The degree of UV protection afforded by a sunscreen composition is directly related to the amount and type of UV filters contained therein. The higher the amount of UV filters, the greater the degree of UV protection. Nevertheless, it is desirable to achieve the best photo protection efficacy with the lowest amount of UV filters. The inventors of the instant disclosure discovered ways to attain SPFs that were not previously attainable with such low amounts of overall UV filters.

SUMMARY OF THE INVENTION

The present disclosure relates to sunscreen compositions that have low amounts of UV filters yet excellent Sun Protection Factors (SPF). Typically, the more UV filters included in a sunscreen composition the higher the SPF. The inventors discovered that when certain UV filters are combined in particular ratios, they interact synergistically to exhibit a surprisingly effective SPF. This allows for use of less UV filters while achieving sufficient SPF.

The present disclosure relates to a sunscreen composition comprising a combination of the UV filters set forth in the table below:

| INCI NAME | TECHNICAL NAME |
|---|---|
| Octocrylene | Octocrylene |
| Butyl Methoxydibenzoylmethane | Avobenzone |
| Bis-EthylHexyloxyphenol Methoxyphenyl Triazine | Tinosorb S |
| Ethylhexyl Triazone | Uvinul T150 |
| Terephthalylidene Dicamphor Sulfonic Acid | Mexoryl SX |
| Drometrizole Trisiloxane | Mexoryl XL |

The ratio of each filter relative to avobenzone in the sunscreen compositions is typically as follows:
the ratio of octocrylene to avobenzone is 0.8:1.0 to 1.5:1.0;
the ratio of Tinosorb S to avobenzone 0.3:1.0 to 0.8:1.0;
the ratio of Uvinul T150 to avobenzone is 0.3:1.0 to 1.0:1.0;
the ratio of Mexoryl SX to avobenzone is 0.1:1.0 to 0.5:1.0; and
the ratio of Mexoryl XL to avobenzone is 0.3:1.0 to 1.0:1.0.

In particular, the ratio of each filter relative to avobenzone is about: 1.2:1.0:0.5:0.6:0.4:0.6 (octocrylene:avobenzone:Tinosorb S:Uvinul T150:Mexoryl SX:Mexoryl XL).

In one embodiment the UV filters are present in the following percentages by weight relative to the entire weight of the sunscreen composition:
2 to 7 wt. % octocrylene;
2 to 5 wt. % avobenzone;
0.1% to 2 wt. % Tinosorb S;
0.1% to 3 wt. % Uvinul T 150;
0.1% to 2 wt. % Mexoryl SX; and
0.1% to 3 wt. % Mexoryl XL.

In another embodiment the UV filters are present in the following percentages by weight relative to the entire weight of the sunscreen composition: about 5% octocrylene; about 4.0% Avobenzone; about 2% Tinosorb S; about 2.5% UvinulT150; about 1.5% MexorylSX; and about 2.5% MexorylXL.

Octisalate is another UV filter than can optionally be included in the sunscreen compositions described herein. If included, octisalate is typically present in an amount greater than 0 to about 5 wt. %.

The present disclosure is also directed to methods of protecting a keratinous substrate from ultraviolet radiation and to methods of absorbing ultraviolet light. Such methods encompass applying a sunscreen composition to a keratinous substrate and subjecting the keratinous substrate to ultraviolet radiation.

DETAILED DESCRIPTION

Where the following terms are used in this specification, they are used as defined below.

The terms "comprising," "having," and "including" are used in their open, non-limiting sense.

The terms "a" and "the" are understood to encompass the plural as well as the singular.

As used herein, the expression "at least one" means one or more and thus includes individual components as well as mixtures/combinations.

"Cosmetically acceptable" means that the item in question is compatible with any keratinous substrate. For example, "cosmetically acceptable carrier" means a carrier that is compatible with any keratinous substrate.

A "physiologically acceptable medium" means a medium which is not toxic and can be applied to the skin, lips, hair, scalp, lashes, brows, nails or any other cutaneous region of the body. The composition of the instant disclosure may especially constitute a cosmetic or dermatological composition.

The phrase "essentially free" refers to less than or equal to 0.5, 0.1, 0.05 or 0.01 wt. %.

The phrase "stable emulsion" refers to a composition that does not undergo phase separation up to a temperature of 45° C. for at least two weeks.

As mentioned above, the present disclosure relates to a sunscreen composition having the following combination of UV filters: octocrylene, avobenzone, Tinosorb S, Uvinul T150, Mexoryl SX, Mexoryl XL; wherein the ratio of each filter relative to avobenzone is as follows:

the ratio of octocrylene to avobenzone is 0.8:1.0 to 1.5:1.0;
the ratio of Tinosorb S to avobenzone 0.3:1.0 to 0.8:1.0;
the ratio of Uvinul T150 to avobenzone is 0.3:1.0 to 1.0:1.0; and
the ratio of Mexoryl SX to avobenzone is 0.1:1.0 to 0.5:1.0
the ratio of Mexoryl XL to avobenzone is 0.3:1.0 to 1.0:1.0

In particular, the ratio of each filter relative to avobenzone is about: 1.2:1.0:0.5:0.6:0.4:0.6 (octocrylene:avobenzone:Tinosorb S:Uvinul T150:Mexoryl SX:Mexoryl XL).

The total amount of the combination of UV filters can vary depending on the desired SPF and overall UV filtering strength of a final sunscreen composition. In one aspect, the total amount of the combination of UV filters in a sunscreen combination is about 50, 40, 30, 25, 20, 19, 18, 17, 16, 15, 14, 13, 12, 11, 10, 9, 8, 7, 6, 5, 4, 3, 2, or 1 wt. % or less. In another aspect, the sunscreen formulation can have an SPF value that is at least about 5, 6, 7, 8, 9, or 10 times the total weight percent of the combination of UV filters of the sunscreen compositions. For example, it is possible for a composition comprising about 17.6 wt. % of a total combination of UV filters to exhibit an SPF of 174.73, as shown in Example 1 below (the SPF is about 9.9 times higher than the total amount of the combination of UV filters used in the composition).

In one embodiment the UV filters are independently present in the following percentages by weight relative to the entire weight of the sunscreen composition:

from about 2, 3, or 4, to about 6, or 7 wt. % octocrylene;
from about 2, 3, or 3.5 to about 4.5 or 5 wt. % avobenzone;
from about 0.1, 0.5, or 1 to about 2, 2.5, or 3 wt. % Tinosorb S;
from about 0.1, 0.5, or 1 to about 2.5, 3, 3.5 or 4 wt. % Uvinul T 150;
from about 0.1, 0.5, or 1, to about 1.5, 2, 2.5, or 3 wt. % Mexoryl SX; and
from about 0.1, 0.5, 1, or 1.5 to about 2, 2.5, or 3 wt. % Mexoryl XL.

In another embodiment the UV filters are present in the following percentages by weight relative to the entire weight of the sunscreen composition:

about 5% octocrylene;
about 4.0% Avobenzone;
about 2% Tinosorb S;
about 2.5% UvinulT150;
about 1.5% MexorylSX; and
about 2.5% MexorylXL.

Octisalate is another UV filter than can optionally be included in the sunscreen compositions described herein. If included, octisalate is typically present in an amount greater than 0 to about 5 wt. %. It may also be present in an amount of about 0.1, 0.5, 1, 1.5, or 2 wt. % to about 2.5, 3, 3.5, 4, 4.5, or 5 wt. %.

The present disclosure makes it possible to achieve the described SPFs in sunscreen compositions without the use of boosters, or essentially free of boosters, e.g., sorbeth-2-hexaoleate. Although boosters may be included in the sunscreen compositions of the instant disclosure, they are not required.

Sunscreen compositions according to the present disclosure can be formulated to achieve a variety of different SPFs. For example, the sunscreen formulations can have an SPF of at least 5, 10, 15, 20, 25, 30, 35, 40, 45, 50, 55, 60, 65, 70, 75, 80, 85, 90, 95, 100, 105, 110, 115, 120, 125, 150, 155, 160, 165, 170, or higher.

The present disclosure is also directed to methods for protecting a keratinous substrate from ultraviolet radiation and to methods of absorbing ultraviolet light. Such methods encompass applying a sunscreen composition to a keratinous substrate and subjecting the keratinous substrate to ultraviolet radiation.

Oils/Emollients

Examples of oils/emollients that may be included in the sunscreen compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane ($C_{11}$) and of n-tridecane ($C_{13}$) sold under the reference Cetiol UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; mixtures thereof.

Additional examples include benzoic acid esters of $C_9$-$C_{15}$ alcohols, isononyl iso-nonanoate, $C_{12}$-$C_{15}$ alkyl benzoate, or any combinations thereof.

Specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl isononanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

Examples of hydrophilic organic solvents that may be included in the sunscreen compositions include:

monohydric $C_1$-$O_8$ alcohols such as ethanol, propanol, butanol, isopropanol, isobutanol;

Polyethylene glycols from 6 to 80 ethylene oxides such as propylene glycol, isoprene glycol, butylene glycol, glycerol, sorbitol;

mono or di-alkyl isosorbides such as dimethyl isosorbide;

Examples of amphiphilic organic solvents include: polypropylene glycol (PPG) like propylene glycol alkyl ester or alkyl ether of PPG like PPG-23 oleyl ether and PPG-36 oleate.

The above lists are only examples and not limiting.

The total amount of oils/emollient present in the compositions is typically about 0.1, 0.5, 1.0, or 2.5 wt. % to about 5.0, 7.5, 10.0, 15.0, 20.0, or 30 wt. % of the total weight of the composition.

Film Formers

Film-formers are often incorporated into sunscreen compositions to ensure even coverage of the UV filters and can be used to render the composition water resistant. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and mixtures thereof. In some cases, the film former is acrylates/$C_{12}$-$C_{22}$ alkylmethacrylate copolymer sold under the tradename Allianz OPT® by ISP.

Many of the common film-forming polymers included in sunscreen compositions are not soluble in ethanol (such as PVP/Eicosene copolymer). A common film-former employed in ethanol based sunscreen products is Dermacryl LT or Dermacryl 79 marketed by Akzo Nobel (INCI Name: acrylates/octylacrylamide copolymner). Dermacryl LT (CAS Number: 80570-62-3) is a hydrophobic, high molecular weight carboxylated acrylic copolymer. It functions as a film-former in a broad range of cosmetic formulations, imparting waterproofing, increased occlusivity and decreased rub-off of actives.

The above lists are only examples and not limiting.

The total amount of film-formers present in the compositions is typically in an amount of about 0.1, 0.5, 1.0, or 5 wt. % to about 5, 10, 20, or 25 wt. %, based on the total weight of the composition.

Emulsifiers

The sunscreen compositions typically include at least one emulsifier such as an amphoteric, anionic, cationic or nonionic emulsifier, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose. The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tego-care 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tegocare CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BB5, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The above lists are only examples and not limiting.

The total amount of emulsifier present in the compositions is typically in an amount of about 0.1, 0.2, or 0.5 wt. % to about 4.0, 5.0, 6.0, or 7.5 wt. %, based on the total weight of the composition.

Gelling Agent

Gelling agents may also be included in the sunscreen compositions. Examples of suitable hydrophilic gelling agents include carboxyvinyl polymers such as the Carbopol products (carbomers) and the Pemulen products (acrylate/C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) (CTFA name: ammonium polyacryldimethyltauramide); cellulose-based derivatives such as hydroxyethyl-cellulose; polysaccharides and especially gums such as xanthan gum; and mixtures thereof.

Lipophilic gelling agents (thickeners) that may be mentioned include modified clays such as hectorite and its derivatives, for instance the products sold under the name bentone.

In some instances, the gelling agent is ammonium acryloyldimethyltaurate/steareth-25 methacrylate crosspolymer, commercially available from Clariant under the tradename Aristoflex HMS.

The above lists are only examples and not limiting.

The gelling agent is typically used in an amount of about 0.05 to about 1.5% by weight, from about 0.08 to about 1.0% by weight, or about 0.1 to about 0.5% by weight, based on the total weight of the composition.

Additional Sunscreen Filters (Protective Agents)

The sunscreen compositions can include additional sunscreen filters such as, for example, mineral UV filters. Examples of mineral UV filters include pigments and nanopigments (mean size of the primary particles is generally is from 5 nm to 100 nm or from 10 nm to 50 nm) of treated or untreated metal oxides such as, for example, nanopigments of titanium oxide (amorphous or crystallized in rutile and/or anatase form), of iron oxide, of zinc oxide, of zirconium oxide or of cerium oxide. The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, polyethylene, silicones, proteins (collagen or elastin), alkanolamines, silicon oxides, metal oxides, sodium hexametaphosphate, alumina or glycerol. The treated nanopigments may more particularly be titanium oxides treated with:

silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide;

alumina and aluminium stearate, such as the product "Microtitanium Dioxide MT 100 T" from the company Tayca;

alumina and aluminium laurate, such as the product "Microtitanium Dioxide MT 100 S" from the company Tayca;

iron oxides and iron stearate, such as the product "Microtitanium Dioxide MT 100 F" from the company Tayca;

silica, alumina and silicone, such as the products "Microtitanium Dioxide MT 100 SAS", "Microtitanium Dioxide MT 600 SAS" and "Microtitanium Dioxide MT 500 SAS" from the company Tayca;

sodium hexametaphosphate, such as the product "Microtitanium Dioxide MT 150 W" from the company Tayca;

octyltrimethoxysilane, such as the product "T-805" from the company Degussa;

alumina and stearic acid, such as the product "UVT-M160" from the company Kemira;

alumina and glycerol, such as the product "UVT-M212" from the company Kemira;

alumina and silicone, such as the product "UVT-M262" from the company Kemira.

Other titanium oxide nanopigments treated with a silicone are $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimethylhydrogenosiloxane and for which the mean size of the elementary particles is 25 nm, such as the product sold under the trade name "Microtitanium Dioxide USP Grade Hydrophobic" by the company Color Techniques.

Uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide nanopigments are, for example:

those sold under the name "Z-Cote" by the company Sunsmart;

those sold under the name "Nanox" by the company Elementis; and those sold under the name "Nanogard WCD 2025" by the company Nanophase Technologies.

The coated zinc oxide nanopigments are, for example:

those sold under the name "Zinc Oxide CS-5" by the company Toshibi (ZnO coated with polymethylhydrogenosiloxane);

those sold under the name "Nanogard Zinc Oxide FN" by the company Nanophase Technologies (as a 40% dispersion in Finsolv TN, $C_{12}$-$C_{15}$ alkyl benzoate);

those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);

those sold under the name "NFD Ultrafine ZNO" by the company Daikin (ZnO coated with perfluoroalkyl phosphate and copolymer based on perfluoroalkylethyl as a dispersion in cyclopentasiloxane);

those sold under the name "SPD-Z1" by the company Shin-Etsu (ZnO coated with silicone-grafted acrylic polymer, dispersed in cyclodimethylsiloxane);

those sold under the name "Escalol Z100" by the company ISP (alumina-treated ZnO dispersed in an ethylhexyl methoxycinnamate/PVP-hexadecene/methicone copolymer mixture);

those sold under the name "Fuji ZNO-SMS-10" by the company Fuji Pigment (ZnO coated with silica and polymethylsilsesquioxane); and those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide" by the company Rhone-Poulenc. The uncoated iron oxide nanopigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220". The coated iron oxide nanopigments are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 BL" or by the company BASF under the name "Transparent Iron Oxide".

Mixtures of metal oxides may also be used, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The above lists are only examples and not limiting.

The compositions according to the instant disclosure may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion.

The instant disclosure will be better understood from the examples that follow, all of which are intended for illustrative purposes only and are not meant to limit the scope of the instant disclosure in any way.

EXAMPLES 1-12

Samples comprising different amounts of UV filters were prepared by dissolving the UV filters in ethanol and solvent as illustrated in the table below.

TABLE 1

| Ingredient | Range |
| --- | --- |
| Octocrylene | 4.40-6.00% |
| Avobenzone | 3.50-4.50% |
| (Butyl Methoxydibenzoylmethane) | |

TABLE 1-continued

| Ingredient | Range |
| --- | --- |
| Tinosorb S | 0.50-2.00% |
| (Bis-EthylHexyloxyphenol Methoxyphenyl Triazine) | |
| UvinulT150 | 0.50-3.00% |
| (Ethylhexyl Triazone) | |
| Mexoryl SX | 1.67-2.00% |
| (Terephthalylidene Dicamphor Sulfonic Acid) | |
| Mexoryl XL | 0.50-3.00% |
| (Drometrizole Trisiloxane) | |
| TEA | 0-1.05% |
| (Triethanolamine) | |
| Polysorbate 20 | 5.50% |
| Propylene Glycol | 5% |
| Eldew SL205 Solvent* | 31.75% |
| Dermacryl 79** | 2.5% |
| Ethanol | Qs 100% |

*Eldew SL 205 (Ajinomoto) is Isopropyl Lauroyl Sarcosinate (emollient)
**Dermacryl 79 (Akzo Nobel) is an acrylate/octylacrylamide Copolymner (film-former)

Each sample was applied to a PMMA plate (polymethyl methacrylate plate) with a draw down bar to control the thickness and the homogeneity of the film. The in vitro SPF was measured using a Labsphere 2000. Each measurement was made 6 times (6 times on each plate) times on 3 plates for each composition. The amount of UV filters included in each sample and the resulting SPF is reported in the table below.

TABLE 2

| No. | Octocrylene | Avobenzone (Butyl Methoxydibenzoylmethane) | Tinosorb S (Bis-EthylHexyloxyphenol Methoxyphenyl Triazine) | Uvinul T150 (Ethylhexyl Triazone) | Mexoryl SX (Terephthalylidene Dicamphor Sulfonic Acid) | Mexoryl XL (Drometrizole Trisiloxane) | Total UV Filters | SPF |
| --- | --- | --- | --- | --- | --- | --- | --- | --- |
| 1 | 4.89 | 4.11 | 1.97 | 2.69 | 1.45 | 2.49 | 17.6 | 174.73 |
| | | | Comparisons | | | | | |
| 2 | 4.40 | 4.00 | 0.50 | 3.00 | 1.00 | 2.50 | 15.40 | 150.27 |
| 3 | 5.88 | 4.84 | 0.68 | 2.83 | 0.95 | 2.84 | 18.02 | 143.96 |
| 4 | 5.21 | 4.97 | 0.65 | 2.87 | 1.71 | 2.90 | 18.31 | 137.67 |
| 5 | 5.73 | 4.89 | 1.35 | 2.28 | 1.04 | 2.86 | 18.15 | 129.53 |
| 6 | 5.54 | 4.63 | 1.29 | 2.42 | 0.98 | 2.76 | 17.62 | 127.34 |
| 7 | 5.97 | 4.61 | 1.35 | 2.74 | 1.87 | 2.87 | 19.41 | 126.63 |
| 8 | 5.88 | 4.71 | 1.20 | 2.94 | 1.08 | 2.85 | 18.66 | 125.59 |
| 9 | 5.50 | 4.47 | 1.12 | 2.71 | 1.49 | 2.63 | 17.92 | 118.71 |
| 10 | 5.44 | 4.33 | 1.11 | 2.74 | 1.41 | 2.89 | 17.92 | 114.16 |
| 11 | 5.85 | 4.77 | 1.10 | 2.72 | 1.62 | 2.83 | 18.89 | 113.10 |
| 12 | 5.61 | 4.98 | 0.96 | 2.85 | 1.76 | 2.43 | 18.59 | 110.52 |
| 13 | 5.20 | 4.50 | 1.00 | 2.50 | 2.00 | 1.00 | 16.20 | 104.97 |
| 14 | 5.61 | 4.85 | 0.80 | 2.59 | 1.99 | 2.59 | 18.43 | 103.34 |
| 15 | 5.87 | 4.81 | 0.86 | 2.57 | 1.64 | 1.99 | 17.74 | 98.61 |
| 16 | 5.60 | 4.00 | 2.00 | 1.00 | 2.00 | 3.00 | 17.60 | 93.87 |
| 17 | 5.31 | 4.99 | 1.76 | 1.28 | 1.90 | 2.91 | 18.15 | 89.81 |
| 18 | 6.00 | 4.50 | 2.00 | 0.50 | 1.67 | 2.50 | 17.17 | 85.00 |
| 19 | 5.97 | 4.73 | 1.81 | 0.53 | 1.79 | 2.83 | 17.66 | 80.88 |
| 20 | 5.60 | 3.50 | 1.00 | 1.50 | 2.00 | 3.00 | 16.60 | 80.45 |
| 21 | 5.59 | 4.26 | 0.94 | 2.98 | 1.99 | 1.95 | 17.71 | 75.70 |
| 22 | 6.00 | 4.00 | 2.00 | 2.00 | 2.00 | 0.50 | 16.50 | 61.57 |
| 23 | 4.80 | 4.00 | 0.50 | 2.50 | 2.00 | 0.50 | 14.30 | 60.01 |

TABLE 2-continued

| No. | Octocrylene | Avobenzone (Butyl Methoxydibenzoylmethane) | Tinosorb S (Bis-EthylHexyloxyphenol Methoxyphenyl Triazine) | Uvinul T150 (Ethylhexyl Triazone) | Mexoryl SX (Terephthalylidene Dicamphor Sulfonic Acid) | Mexoryl XL (Drometrizole Trisiloxane) | Total UV Filters | SPF |
|---|---|---|---|---|---|---|---|---|
| 24 | 5.60 | 4.00 | 1.00 | 1.50 | 2.00 | 2.00 | 16.10 | 56.14 |
| 25 | 4.80 | 3.50 | 1.00 | 2.00 | 1.67 | 3.00 | 15.97 | 51.68 |

The following table corresponds to the table above (TABLE 2) but lists each UV filter as a ratio relative to avobenzone.

TABLE 3

| No. | Octocrylene | Avobenzone (Butyl Methoxydibenzoylmethane) | Tinosorb S (Bis-EthylHexyloxyphenol Methoxyphenyl Triazine) | Uvinul T150 (Ethylhexyl Triazone) | Mexoryl SX (Terephthalylidene Dicamphor Sulfonic Acid) | Mexoryl XL (Drometrizole Trisiloxane) | Total UV Filters | SPF |
|---|---|---|---|---|---|---|---|---|
| 1 | 1.19 | 1.00 | 0.48 | 0.65 | 0.35 | 0.61 | 17.6 | 174.73 |
| Comparisons | | | | | | | | |
| 2 | 1.10 | 1.00 | 0.13 | 0.75 | 0.25 | 0.63 | 15.40 | 150.27 |
| 3 | 1.21 | 1.00 | 0.14 | 0.58 | 0.20 | 0.59 | 18.02 | 143.96 |
| 4 | 1.05 | 1.00 | 0.13 | 0.58 | 0.34 | 0.58 | 18.31 | 137.67 |
| 5 | 1.17 | 1.00 | 0.28 | 0.47 | 0.21 | 0.58 | 18.15 | 129.53 |
| 6 | 1.20 | 1.00 | 0.28 | 0.52 | 0.21 | 0.60 | 17.62 | 127.34 |
| 7 | 1.30 | 1.00 | 0.29 | 0.59 | 0.40 | 0.62 | 19.41 | 126.63 |
| 8 | 1.25 | 1.00 | 0.25 | 0.62 | 0.23 | 0.61 | 18.66 | 125.59 |
| 9 | 1.23 | 1.00 | 0.25 | 0.61 | 0.33 | 0.59 | 17.92 | 118.71 |
| 10 | 1.26 | 1.00 | 0.26 | 0.63 | 0.32 | 0.67 | 17.92 | 114.16 |
| 11 | 1.23 | 1.00 | 0.23 | 0.57 | 0.34 | 0.59 | 18.89 | 113.10 |
| 12 | 1.13 | 1.00 | 0.19 | 0.57 | 0.35 | 0.49 | 18.59 | 110.52 |
| 13 | 1.16 | 1.00 | 0.22 | 0.56 | 0.44 | 0.22 | 16.20 | 104.97 |
| 14 | 1.16 | 1.00 | 0.16 | 0.53 | 0.41 | 0.53 | 18.43 | 103.34 |
| 15 | 1.22 | 1.00 | 0.18 | 0.53 | 0.34 | 0.41 | 17.74 | 98.61 |
| 16 | 1.40 | 1.00 | 0.50 | 0.25 | 0.50 | 0.75 | 17.60 | 93.87 |
| 17 | 1.06 | 1.00 | 0.35 | 0.26 | 0.38 | 0.58 | 18.15 | 89.81 |
| 18 | 1.33 | 1.00 | 0.44 | 0.11 | 0.37 | 0.56 | 17.17 | 85.00 |
| 19 | 1.26 | 1.00 | 0.38 | 0.11 | 0.38 | 0.60 | 17.66 | 80.88 |
| 20 | 1.60 | 1.00 | 0.29 | 0.43 | 0.57 | 0.86 | 16.60 | 80.45 |
| 21 | 1.31 | 1.00 | 0.22 | 0.70 | 0.47 | 0.46 | 17.71 | 75.70 |
| 22 | 1.50 | 1.00 | 0.50 | 0.50 | 0.50 | 0.13 | 16.50 | 61.57 |
| 23 | 1.20 | 1.00 | 0.13 | 0.63 | 0.50 | 0.13 | 14.30 | 60.01 |
| 24 | 1.40 | 1.00 | 0.25 | 0.37 | 0.50 | 0.50 | 16.10 | 56.14 |
| 25 | 1.37 | 1.00 | 0.29 | 0.57 | 0.48 | 0.86 | 15.97 | 51.68 |

*NOTE:
The bolded numbers fall outside the claimed range.

As illustrated in the tables above, Example 1, having a ratio of about 1.2:1.0:0.5:0.6:0.4:0.6 (Octocylene:Avobenzone:Tinosorb S:Uvinul T 150:Mexoryl SX, Mexoryl XL) shows an dramatic jump in SPF.

EXAMPLE 13

Using the procedures described above for Examples 1-12, the following composition was prepared and the SPF measured.

TABLE 4

| Clear Spray-On Sunscreen SPF 175 (In Vitro) | |
|---|---|
| Ingredient | Range |
| Octocrylene | 4.89% |
| Avobenzone | 4.11% |
| Tinosorb S | 1.97% |
| UvinulT150 | 2.69% |
| Mexoryl SX | 1.45% |
| Mexoryl XL | 2.49% |
| TEA | 0.76% |
| Polysorbate 20 | 5.50% |
| Propylene Glycol | 5% |
| Eldew SL205 Solvent* | 31.75% |
| Dermacryl 79** | 2.5% |
| Ethanol | Qs 100% |

*Eldew SL 205 (Ajinomoto) is Isopropyl Lauroyl Sarcosinate (emollient)
**Dermacryl 79 (Akzo Nobel) is an acrylate/octylacrylamide Copolymner (film-former)

EXAMPLE 14

The following composition was prepared and the SPF measured.

TABLE 5

Lotion Sunscreen Spray

| Phase | Chemical Name | % wt/wt |
|---|---|---|
| A-1 | Water | Q.S. |
|  | Preservative | 0.1 to 2.00 |
|  | Disodium EDTA | 0.100 |
|  | O/W emulsifier | 0.1 to 2.00 |
| A-2 | Mexoryl Sx | 1.45 |
|  | TEA | 0.650 |
| B | Avobenzone | 4.110 |
|  | Octocrylene | 4.890 |
|  | Uvinul T-150 | 2.690 |
|  | Mexoryl XL | 2.490 |
|  | Tinosorb S | 1.970 |
|  | Emollient | 2.0-20.0 |
|  | Silicone | 1.0-3.0 |
|  | W/O emulsifier | 0.1-2.5 |
|  | Co-emulsifier | 0.1-2.0 |
|  | Vit E | 0.100 |
| C | Water | 7.000 |
|  | Silicone | 1.0-5.0 |
| D | Booster | 1.0-6.0 |
| E | Wetting Agent | 0.1-1.5 |

The components of the Lotion Sunscreen were combined as outlined below.
1) Weigh Phase A and heat to 85° C.
2) Weigh Phase B ingredients in another beaker and heat to 85° C.
3) Add Phase B into Phase A and homogenized for 20 minutes. Maintain the temperature at 90° C.
4) Check emulsion quality. If emulsion quality is good then begin cooling to room temperature.
5) Add Phase C into Phase A/B and homogenize for 5 minutes.
6) Pass the emulsion through a high pressure homogenizer two times at 500 bar.
7) Add phase D at room temperature and mix for 5 minutes.

It is claimed:

1. A sunscreen composition comprising the following combination of UV filters: octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane; wherein the ratio of each filter relative to butyl methoxydibenzoylmethane is as follows:
   the ratio of octocrylene to butyl methoxydibenzoylmethane is 0.8:1.0 to 1.5:1.0;
   the ratio of bis-ethylhexyloxyphenol methoxyphenyl triazine to butyl methoxydibenzoylmethane 0.3:1.0 to 0.8:1.0;
   the ratio of ethylhexyl triazone to butyl methoxydibenzoylmethane is 0.3:1.0 to 1.0:1.0;
   the ratio of terephthalylidene dicamphor sulfonic acid to butyl methoxydibenzoylmethane is 0.1:1.0 to 0.5:1.0; and
   the ratio of drometrizole trisiloxane to butyl methoxydibenzoylmethane is 0.3:1.0 to 1.0:1.0.

2. The sunscreen composition according to claim 1, wherein the ratio of each filter relative to butyl methoxydibenzoylmethane is about 1.2:1.0:0.5:0.6:0.4:0.6 (octocrylene:butyl methoxydibenzoylmethane:bis-ethylhexyloxyphenol methoxyphenyl triazine:ethylhexyl triazone:terephthalylidene dicamphor sulfonic acid:drometrizole trisiloxane).

3. The sunscreen composition according to claim 1 having an SPF of at least 15.

4. The sunscreen composition according to claim 1 having an SPF of at least 30.

5. The sunscreen composition according to claim 1 having an SPF of at least 50.

6. The sunscreen composition according to claim 1 having an SPF of at least 75.

7. The sunscreen composition according to claim 1 having an SPF of at least 100.

8. The sunscreen composition according to claim 1 having an SPF of at least 125.

9. The sunscreen composition according to claim 1 having an SPF of at least 150.

10. The sunscreen composition according to claim 1 comprising:
   2 to 7 wt. % octocrylene;
   2 to 5 wt. % butyl methoxydibenzoylmethane;
   0.1% to 2 wt. % bis-ethylhexyloxyphenol methoxyphenyl triazine;
   0.1% to 3 wt. % ethylhexyl triazone;
   0.1% to 2 wt. % terephthalylidene dicamphor sulfonic acid; and
   0.1% to 3 wt. % drometrizole trisiloxane.

11. The sunscreen composition according to claim 1 comprising:
   about 5 wt. % octocrylene;
   about 4 wt. % butyl methoxydibenzoylmethane;
   about 2 wt. % bis-ethylhexyloxyphenol methoxyphenyl triazine;
   about 2.5 wt. % ethylhexyl triazone;
   about 1.5 wt. % terephthalylidene dicamphor sulfonic acid; and
   about 2.5% drometrizole trisiloxane.

12. The sunscreen composition according to claim 1, further comprising a booster.

13. The sunscreen composition according to claim 1, further comprising octisalate.

14. The sunscreen composition according to claim 13, wherein the octisalate is present in an amount greater than 0 to about 5 wt. %, based on the total weight of the sunscreen composition.

15. A method of protecting a keratinous substrate from ultraviolet radiation comprising applying a sunscreen composition according to claim 1 to the keratinous substrate.

16. A method of absorbing ultraviolet light comprising applying a sunscreen composition according to claim 1 to a keratinous substrate and subjecting the keratinous substrate to ultraviolet light.

17. A clear sunscreen composition according to claim 1.

18. A spray-on sunscreen composition according to claim 1.

19. A clear sunscreen composition comprising:
   2 to 7 wt. % octocrylene;
   2 to 5 wt. % butyl methoxydibenzoylmethane;
   0.1% to 2 wt. % bis-ethylhexyloxyphenol methoxyphenyl triazine;
   0.1% to 3 wt. % ethylhexyl triazone;
   0.1% to 2 wt. % terephthalylidene dicamphor sulfonic acid; and
   0.1% to 3 wt. % drometrizole trisiloxane;
   wherein the ratio of each filter relative to butyl methoxydibenzoylmethane is as follows:
   the ratio of octocrylene to butyl methoxydibenzoylmethane is 0.8:1.0 to 1.5:1.0;
   the ratio of bis-ethylhexyloxyphenol methoxyphenyl triazine to butyl methoxydibenzoylmethane 0.3:1.0 to 0.8:1.0;

the ratio of ethylhexyl triazone to butyl methoxydibenzoylmethane is 0.3:1.0 to 1.0:1.0;

the ratio of terephthalylidene dicamphor sulfonic acid to butyl methoxydibenzoylmethane is 0.1:1.0 to 0.5:1.0; and the ratio of drometrizole trisiloxane to butyl methoxydibenzoylmethane is 0.3:1.0 to 1.0:1.0.

20. The sunscreen composition according to claim 19, wherein the ratio of each filter relative to butyl methoxydibenzoylmethane is about 1.2:1.0:0.5:0.6:0.4:0.6 (octocrylene: butyl methoxydibenzoylmethane:bis-ethylhexyloxyphenol methoxyphenyl triazine:ethylhexyl triazone:terephthalylidene dicamphor sulfonic acid:drometrizole trisiloxane).

* * * * *